United States Patent
Taub et al.

(10) Patent No.: US 11,589,954 B2
(45) Date of Patent: **\*Feb. 28, 2023**

(54) METHOD AND SYSTEM FOR DESIGNING AND PRODUCING DENTAL PROSTHESIS AND APPLIANCES

(71) Applicant: Align Technology, Inc., San Jose, CA (US)

(72) Inventors: Eldad Taub, Reut (IL); Avi Kopelman, Palo Alto, CA (US)

(73) Assignee: Align Technology, Inc., San Jose, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 17/534,254

(22) Filed: Nov. 23, 2021

(65) Prior Publication Data

US 2022/0079712 A1 Mar. 17, 2022

Related U.S. Application Data

(63) Continuation of application No. 15/371,005, filed on Dec. 6, 2016, now Pat. No. 11,207,156, which is a continuation of application No. 14/061,598, filed on Oct. 23, 2013, now Pat. No. 9,539,071, which is a continuation of application No. 13/399,866, filed on Feb. 17, 2012, now Pat. No. 8,577,493, which is a continuation of application No. 12/789,573, filed on May 28, 2010, now Pat. No. 8,145,340, which is a continuation of application No. 12/007,015, filed on
(Continued)

(51) Int. Cl.
*A61C 5/77* (2017.01)
*A61C 5/73* (2017.01)
*G16H 20/40* (2018.01)
*G05B 19/042* (2006.01)
*A61C 13/00* (2006.01)
*A61C 9/00* (2006.01)
*A61C 13/34* (2006.01)
*B33Y 80/00* (2015.01)
*A61C 7/00* (2006.01)
*A61C 8/00* (2006.01)
*A61C 13/09* (2006.01)

(52) U.S. Cl.
CPC .............. *A61C 5/77* (2017.02); *A61C 5/73* (2017.02); *A61C 9/0053* (2013.01); *A61C 13/0006* (2013.01); *A61C 13/34* (2013.01); *G05B 19/0421* (2013.01); *G16H 20/40* (2018.01); *A61C 7/002* (2013.01); *A61C 8/0048* (2013.01); *A61C 13/09* (2013.01); *B33Y 80/00* (2014.12); *Y10T 29/49567* (2015.01)

(58) Field of Classification Search
None
See application file for complete search history.

(56) References Cited

U.S. PATENT DOCUMENTS 6,334,853 B1 1/2002 Kopelman et al.
6,845,175 B2 1/2005 Kopelman et al.
(Continued)

*Primary Examiner* — Sean Shechtman
(74) *Attorney, Agent, or Firm* — Wilson Sonsini Goodrich & Rosati

(57) ABSTRACT

A virtual model of an intraoral cavity is provided, wherein this process is initialized by a dental clinic, and the design and manufacture of a suitable dental prosthesis for the intraoral cavity is shared between a dental lab and a service center.

20 Claims, 7 Drawing Sheets

Related U.S. Application Data

Jan. 4, 2008, now Pat. No. 7,738,989, which is a continuation-in-part of application No. 11/062,622, filed on Feb. 23, 2005, now Pat. No. 7,333,874.

(60) Provisional application No. 60/546,946, filed on Feb. 24, 2004.

(56) References Cited

U.S. PATENT DOCUMENTS

| | | |
|---|---|---|
| 6,957,118 B2 | 10/2005 | Kopelman et al. |
| 7,220,124 B2 | 5/2007 | Taub et al. |
| 7,236,842 B2 | 6/2007 | Kopelman et al. |
| 7,361,020 B2 | 4/2008 | Abolfathi et al. |
| 7,442,040 B2 | 10/2008 | Kuo |
| 7,555,403 B2 | 6/2009 | Kopelman et al. |
| 7,766,658 B2 | 8/2010 | Tricca et al. |
| 7,862,336 B2 | 1/2011 | Kopelman et al. |
| 7,871,269 B2 | 1/2011 | Wu et al. |
| 7,947,508 B2 | 5/2011 | Tricca et al. |
| 8,092,215 B2 | 1/2012 | Stone-Collonge et al. |
| 8,244,028 B2 | 8/2012 | Kuo et al. |
| 8,382,474 B2 | 2/2013 | Boltanski et al. |
| 8,509,932 B2 | 8/2013 | Kopelman |
| 8,807,999 B2 | 8/2014 | Kuo et al. |
| 9,375,298 B2 | 6/2016 | Boronkay et al. |
| 9,408,679 B2 | 8/2016 | Kopelman |
| 9,492,243 B2 | 11/2016 | Kuo |
| 9,763,758 B2 | 9/2017 | Kopelman |
| 10,016,262 B2 | 7/2018 | Sabina et al. |
| 10,623,707 B2 | 4/2020 | Greenberg |
| 10,952,816 B2 | 3/2021 | Kopelman |
| 2004/0133293 A1* | 7/2004 | Durbin .......... A61C 13/34 700/98 |
| 2004/0197728 A1* | 10/2004 | Abolfathi .......... A61C 7/00 433/24 |
| 2005/0106529 A1 | 5/2005 | Abolfathi et al. |
| 2006/0115785 A1 | 6/2006 | Li et al. |
| 2008/0138767 A1 | 6/2008 | Kuo et al. |
| 2008/0286716 A1 | 11/2008 | Sherwood |
| 2008/0286717 A1 | 11/2008 | Sherwood |

* cited by examiner

METHOD AND SYSTEM FOR DESIGNING AND PRODUCING DENTAL PROSTHESIS AND APPLIANCES

CROSS-REFERENCE

This application is a continuation application of U.S. patent application Ser. No. 15/371,005, filed Dec. 6, 2016, now U.S. Pat. No. 11,207,156, issued Dec. 28, 2021, which is a continuation of U.S. patent application Ser. No. 14/061, 598, filed Oct. 23, 2013, now U.S. Pat. No. 9,539,071, issued Jan. 10, 2017, which is a continuation of U.S. patent application Ser. No. 13/399,866, filed Feb. 17, 2012, now U.S. Pat. No. 8,577,493, issued Nov. 5, 2013, which is a continuation of U.S. patent application Ser. No. 12/789,573, filed May 28, 2010, now U.S. Pat. No. 8,145,340, issued Mar. 27, 2012, which is a continuation of U.S. patent application Ser. No. 12/007,015, filed Jan. 4, 2008, now U.S. Pat. No. 7,738,989, issued Jun. 15, 2010, which is a continuation of U.S. patent application Ser. No. 11/062,622, filed on Feb. 23, 2005, now U.S. Pat. No. 7,333,874, issued Feb. 19, 2008, which claims the benefit under 35 USC § 119(e) of U.S. Provisional Application No. 60/546,946, filed Feb. 24, 2004, the entire content of each of which is herein incorporated by reference.

FIELD OF THE INVENTION

This invention relates to methods and systems for designing and producing dental prostheses and appliances, and to dental prostheses and appliances produced thereby. In particular, the present invention is concerned with such systems in which a plurality of different work centers linked to a dental clinic utilize a common 3D database each for planning, designing and manufacturing at least parts of such prostheses and appliances.

BACKGROUND OF THE INVENTION

A dental treatment often begins with obtaining a three-dimensional (3D) model of a patient's teeth. The model may be a physical model of the dentition or a virtual 3D computer model. The model is used to assist in designing a dental treatment for the patient. After the treatment has been designed, the model is used to design the dental prosthesis or appliance to be applied to the teeth in order to execute the treatment. Such prostheses and appliances include, for example, bridges, crowns, and orthodontic braces.

In some instances, a negative cast of the dentition is obtained at the dental clinic in which the patient is seen, and may include both arches, one arch or part of an arch. The cast is sent to a dental laboratory, and a positive physical model of the dentition is made from the negative cast, typically by pouring plaster into the cast allowing the plaster to set. A dental treatment is then determined at the clinic using the model, and prostheses or appliances for mounting onto the patient's teeth are designed or selected in order to execute the treatment. The appliances are made at a laboratory and then dispatched to the clinic for mounting onto the patient's teeth.

It is also known to obtain a 3D virtual representation of the teeth that is used to assist in devising a dental treatment and/or to design dental appliances. The 3D computer model may be obtained at the dental clinic using an optical scanner to scan the teeth directly or to scan a model of the teeth. The computer model is then used at the clinic for designing or selecting appropriate dental prosthesis and/or appliances to carry out the treatment. Instructions are then sent to a dental appliance laboratory for making the prosthesis or appliances, which are made at the laboratory and then dispatched to the clinic.

Alternatively, a negative cast of the dentition of each jaw is obtained at a dental clinic that is dispatched to a dental appliance laboratory where a 3D positive model of the patient's teeth is made from the negative cast. The 3D model is then scanned at the laboratory so as to generate a virtual 3D model of the patient's teeth that is used to design appropriate dental prosthesis or appliances. The prosthesis or appliances are produced at the laboratory and then dispatched to the clinic.

U.S. Pat. No. 6,632,089 to Rubbert et al., discloses a computer-based dental treatment planning method. A virtual 3D model of the dentition of a patient is obtained that is used to plan a dental treatment. Obtaining the 3D model as well as treatment planning can be performed at a dental clinic or at a remote location such as a dental appliance laboratory having access to the virtual model of the dentition. In the latter situation, the proposed treatment plan is sent to the clinic for review, and modification or approval by the dentist, before the requisite appliances are made at the laboratory.

SUMMARY OF THE INVENTION

The present invention provides a system and method for designing and producing dental prostheses, such as for example crowns and bridges. The system comprises at least one dental clinic and at least one dental laboratory. The system also comprises a dental service center that is a separate entity with respect to the dental laboratory. The service center is equipped to generate a virtual 3D model (also referred to herein as a "3D numerical model", "numerical model" "virtual model", and the like) of a patient's teeth from data obtained either by scanning (typically optically) the teeth directly or by scanning a physical model of the teeth, the process being at least initiated at the dental clinic. Alternatively, the dental lab may generate the virtual model. The service center is also equipped to use the computer model to design a dental treatment and to select or design and to manufacture dental prostheses, or at least a part thereof. The details of the required prosthesis may then be sent to the clinic, and typically part of the manufacture of the prosthesis is handled by the service center. The dental lab may also be equipped to design at least a part of the prosthesis, typically a coping, for example by first defining the finish line on the 3D model. Alternatively, the dental lab may provide a prescription to the service center for the latter to design the coping. The clinic may then send instructions to a dental laboratory and/or to the service center, each of which is equipped to make a part of the dental prosthesis in accordance with instructions and data received and/or generated from any one of the dental clinic, dental lab or from the service center, and the manufactured prosthesis is then dispatched to the clinic.

In a preferred embodiment, communication between the clinics, laboratories and the service center is over an electronic communications network such as the Internet or other suitable communications medium such as an intranet, local access network, public switched telephone network, cable network, etc.

At least a part of the manufacturing of the prosthesis is shared between the service center and one or more dental labs, according to predetermined criteria. Further, at least one of the service center and the at least one said dental lab is adapted for designing said prosthesis based on the 3D numerical model of the dentition, wherein said prosthesis comprises an inner surface and an outer surface, wherein to provide a 3D model of said prosthesis. The service center is adapted for manufacturing at least a first portion of said prosthesis based on said 3D numerical model. In particular, the service center is adapted for manufacturing at least an internal surface of said prosthesis, wherein said internal surface is designed for mounting onto a target site comprised in said dentition. The prosthesis typically comprises at least one coping and the aforesaid internal surface is an internal surface of said coping. At least one of the service center and the at least one said dental lab is adapted for designing an external surface of said coping based on said 3D numerical model.

Preferably, the service center comprises a material removal machine for directly manufacturing said coping from a suitable coping material based on the design of said internal surface and said external surface of said coping. Alternatively, the material removal machine may be used for manufacturing a physical model of said coping from a suitable wax material or the like based on the design of said internal surface and said external surface of said coping. The service center and/or at least one dental lab, and/or an external facility, comprises means for producing a negative cast of said physical model, and means for producing said coping from said negative model using a suitable coping material.

At least one said dental lab is adapted for manufacturing at least a second portion of said prosthesis based on said 3D numerical model. The dental lab is adapted for manufacturing at least an external surface of said prosthesis, wherein the external surface is designed for providing adequate clearance for the prosthesis relative to other teeth in said dentition adjacent to said prosthesis. Furthermore, the external surface is designed for providing adequate occlusion between the prosthesis relative to other teeth in said dentition opposite to said prosthesis.

The external portion of the prosthesis may be manufactured by a process involving adding at least one layer of material to a suitable coping and subjecting the layer to a material removal operation so that the surface of the layer conforms to a predetermined geometry. A plurality of layers may be sequentially formed over said coping, such that a final said layer conforms to the external surface required for the prosthesis.

Optionally, the fabrication of each layer, or of the layer (when the prosthesis only comprises a single layer), of the prosthesis may be performed using traditional methods. Such traditional methods are known in the art, and include, for example, building porcelain or any other suitable material layer by layer, starting with a first layer laid over the coping, and manually working these layers to fit within the space allowed for the prosthesis in the intra-oral cavity. To facilitate this, a physical (typically plaster or stone) model of at least a part of the intraoral cavity can be produced, typically by the service center and based on the 3D virtual model of the teeth, and this is sent to the dental lab.

Additionally or alternatively, the fabrication of said layer or layers is at least partially automated, and at least one dental lab comprises a material removal machine for removing material from said layer, and suitable scanning means for determining the topology of said layer prior to the material removing operation. Computer means are also provided for calculating machining paths for said material removal machine, wherein such paths are based on the difference between said topology of said layer prior to the material removing operation and the required topology for the surface.

The aforementioned predetermined parameters include a dimensional accuracy for the manufacture of a part of said prosthesis. In particular, when the dimensional accuracy for the manufacture of a particular part is required to be about 40 microns or less than 40 microns, for example the internal surface of the coping, the part is manufactured by said service center. Alternatively, when the dimensional accuracy for a particular part is required to be within substantially more than 40 microns, for example an external part of the crown, this part is manufactured by a dental lab.

In one particular application of the invention, a scan of the intraoral cavity is taken at a dental clinic, and the virtual model data thus obtained is sent to a dental lab. Then, the dental lab defines the margin line of the preparation (in the virtual model) and designs the coping geometry. Alternatively, the virtual model is (also) sent to the service center, together with a suitable prescription from the dental lab, in which case the service center defines the margin line of the preparation (in the virtual model) and designs the coping geometry. In either case, the coping geometry is processed by the service center, which then produces a coping based on the design, either directly, or indirectly via a lost wax process, for example. The coping, together with a physical positive model of the dentition, or a part thereof comprising the preparation, is sent to the dental lab, wherein the technician there prepares the full prosthesis in a traditional manner, by sequentially adding one or more layers of porcelain or other suitable material to the coping, and shaping the layers to produce the outer form of the prosthesis, checking with the physical model that the prosthesis will fit in the space left for it and provide adequate occlusion. The prosthesis is then sent to the dental clinic to be fitted to the patient.

Full flexibility in communication between the clinics, laboratories and the service center is provided, enabling for example, many different communications to be performed therebetween, including the following non-limiting illustrative examples:

(i) scanned data of the intraoral cavity (from which a virtual model thereof is generated) is sent from the dental clinic to the dental lab and/or service center;

(ii) 3D numerical data (i.e., the virtual model) of the intraoral cavity, created directly at the dental lab or service center, or indirectly from data transmitted to either location, is transmitted to the dental clinic for approval;

(iii) approved 3D numerical data of the intraoral cavity, wherever created, is transmitted to the dental lab and/or to the service center;

(iv) definition of the margin line by means of the dental lab or the service center is sent to the dental clinic for approval;

(v) approved margin line definition is sent to the service center and/or dental lab from the dental clinic;

(vi) definition of the 3D coping geometry by means of the dental lab or the service center is sent to the dental clinic for approval;

(vii) approved 3D coping geometry, and/or approval thereof, is sent to the service center and/or dental lab from the dental clinic;

(viii) prescription for the coping is sent from the dental lab to the dental clinic for approval, and approved prescription is sent to dental lab and/or service center.

Herein, "dental clinic" refers to the interface between a dental practitioner and a patient, and thus includes any physical entity, in particular a clinic, in which there is interaction between a dental patient and a dental practitioner. While "dental practitioner" typically refers to a dentist, doctor, prosthodontist or orthodontist, it also includes herein all other caregivers that may interact with a dental patient during the course of a dental treatment. While "dental patient" typically refers to a person requiring the dental services of a dental practitioner, it also includes herein any person regarding whom it is desired to create a 3D numerical model of the intra oral cavity thereof, for example for the purpose of practicing the same or for carrying out research.

The term "prosthesis" is herein taken to include any restoration and any onlays, such as crowns and bridges, for example, and inlays, such as caps, for example, and any other artificial partial or complete denture.

The terms virtual model, 3D numerical model, and the like, are used interchangeably herein to refer to a computer simulation of a surface, comprising 3D topographic data referring to the surface, such a surface typically being dental surfaces of the intraoral cavity.

In another aspect of the invention a system and method are provided for designing and producing dental appliances, such as for example braces. The system comprises at least one dental clinic and at least one dental laboratory. The system also comprises a dental service center that is separate from the dental laboratory. The service center is equipped to generate a virtual 3D model of a patient's teeth from data obtained either by optically scanning the teeth directly or by scanning a physical model of the teeth, the process being at least initiated at the dental clinic. Alternatively, the dental lab may generate the virtual model. The service center is also equipped to use the computer model to design a dental treatment and to select or design and to manufacture appliances to carry out the treatment. The details of the treatment and of the required appliances may be then sent to the clinic. The clinic may then send instructions to a dental laboratory which is equipped to make at least a part of the dental appliances in accordance with instructions received from either a dental clinic or from the service center, and the appliances are then dispatched to the clinic.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
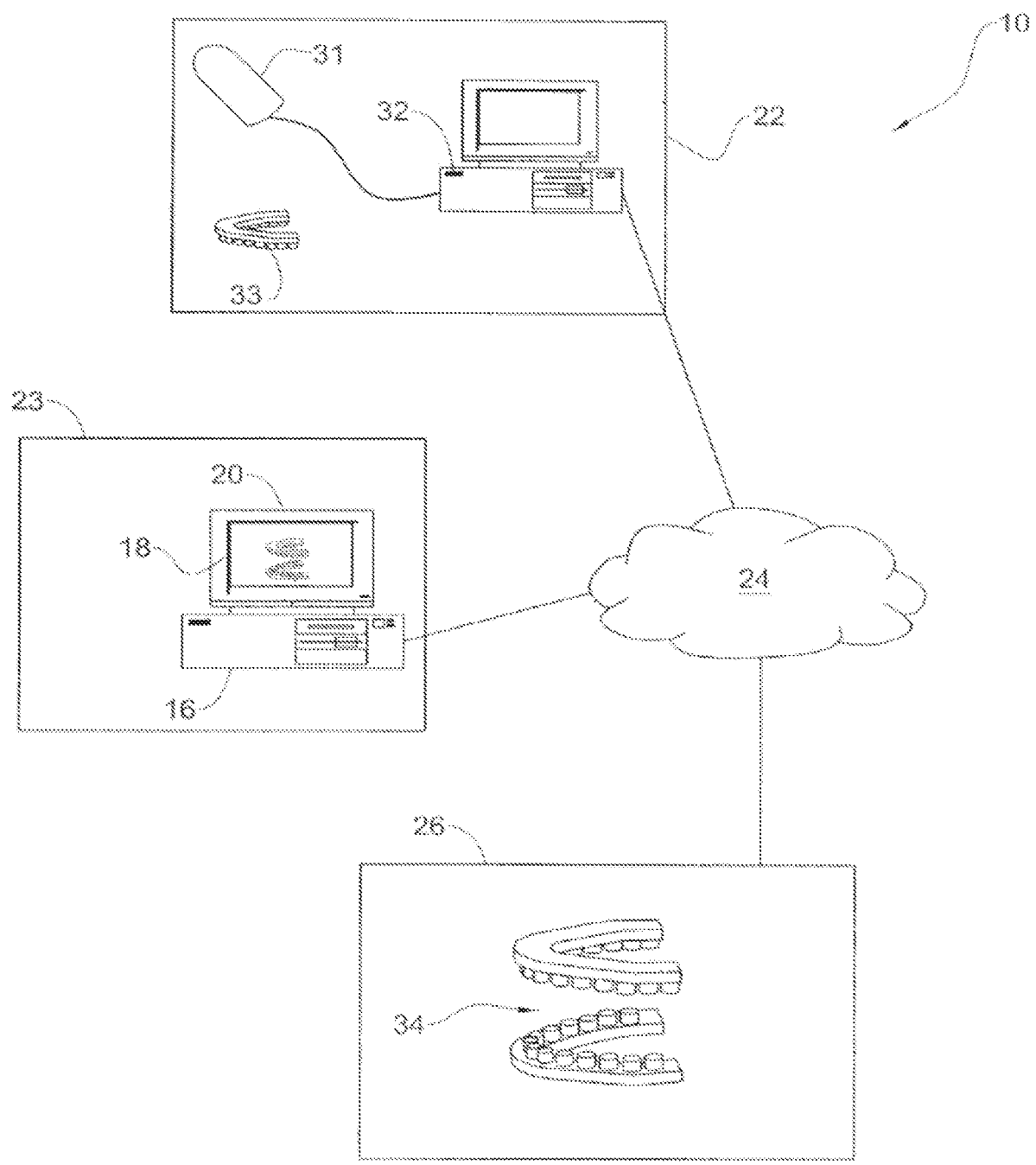
FIG. 1 shows a dental service system for designing and producing dental appliances in accordance with one embodiment of one aspect of the invention.

FIG. 1 illustrates a system 10 for designing and producing dental appliances, in accordance with the invention. The system 10 comprises a dental service center 23, one or more dental clinics 22, and one or more dental labs 26. The dental clinics 22 and the dental labs 26 are linked to each other and each to the dental service center 23 via a communication means or network such as for example the Internet or other suitable communications medium such as an intranet, local access network, public switched telephone network, cable network, satellite communication system, and the like, indicated by the cloud at 24. Optionally, it is also possible for some dental clinics 22 to be linked to each other, and/or for some dental labs 26 to be linked to each other, via the same one or a different one of said communication medium, for example when such dental clinics or labs form part of a common commercial entity. Further optionally, such interlinked dental clinics 22 and/or dental labs 26 may be further linked with other entities, for example a head clinic or head lab, comprising a centralized data base (not shown).

According to the invention, digitised three-dimensional (3D) information W (FIG. 2) of the patient's intra-oral cavity, or part thereof, is created by the system, and this information is then used by the dental labs 26 and/or the service center 23 for designing and/or manufacturing a custom dental prosthesis in an optimal and cost efficient manner. Accordingly, acquiring an accurate 3D representation of the intraoral cavity is the first step that is carried out by the system. Typically, the 3D information is obtained at the clinic 22, but this information may be obtained, alternatively, by one of the dental labs 26 or the service centre 23, as described herein.

Preferably, each dental clinic 22 may provide the 3D digitized data of the intraoral cavity, including the dentition and associated anatomical structures of a patient, and thus comprises suitable equipment for scanning a patient's teeth. Such equipment may include, for example, a hand-held scanner 31 that is used by the practitioner to acquire the 3D data. Advantageously, a probe for determining three dimensional structure by confocal focusing of an array of light beams may be used, for example as manufactured under the name of PROSTHOCAD or as disclosed in WO 00/08415, the contents of which are incorporated herein by reference in their entirety. The 3D data obtained by the probe may then be stored in a suitable storage medium, for example a memory in a computer workstation 32, before being sent over the communication network 24 to the dental service center 23 and/or to the dental lab 26, for further processing, as described below.

Alternatively, each clinic 22 may include equipment for obtaining a negative casting of a patient's teeth. In this case, the negative cast or impression is taken of the patient's teeth, in a manner known in the art, and this negative model 33 is dispatched to one of the dental labs 26 that is equipped to prepare from the negative model a positive cast 34 suitable for scanning. The positive cast 34 may be scanned at the dental lab 26 by any method known in the art, including using the aforesaid probe manufactured under the name of PROSTHOCAD or as disclosed in WO 00/08415. The 3D data is then transmitted over the network 24 to the service center 23. Alternatively, the positive cast 34 may be dispatched to the service center 23 by the dental clinic 22 and scanned at the service center to obtain the 3D data. Alternatively, the service center 23 produces a positive model 34 from the negative model 33 and is scanned thereat or sent to the dental clinic 22 to be scanned thereat. Alternatively, the negative model 33 is scanned, either at the dental lab 26 or at the service center 23.

Alternatively, the negative model 33 provided by the clinic 22 is sent to the service center 23, either directly by the clinic 22, or indirectly via the dental lab 26, and a composite positive-negative model may be manufactured from the original negative model. Thereafter, the positive-negative model may be processed to obtain 3D digitized data, for example as disclosed in U.S. Pat. No. 6,099,314, assigned to the present assignee, and the contents of which are incorporated herein in their entirety.

Alternatively, the 3D digitized data may be obtained in any other suitable manner, including other suitable intra oral scanning techniques, based on optical methods, direct contact or any other means, applied directly to the patient's dentition. Alternatively, X-ray based, CT based, Mill based, or any other type of scanning of the patient or of a positive and/or negative model of the intra-oral cavity may be used. The dimensional data may be associated with a complete dentition, or of a partial dentition, for example such as a preparation only of the intra oral cavity.

Once the 3D digitized data is obtained, the next step is to design the dental prosthesis in question, followed by the manufacture thereof, and finally the installation of the appliance in the oral cavity of the patient.

The design and the manufacture of the appliance may each be carried out at the dental lab 26 or at the service centre 23, or alternatively one or both of these activities may be shared between the two; in each case the design and manufacture are based on the original 3D data of the oral cavity previously obtained.

The dental lab 26 comprises a laboratory, or a design or manufacturing entity that provides direct technical services to the dental clinic 22. Such services include, for example, scanning, manufacturing, analyzing the preparation in the intra oral cavity to mark the location of the finish line, for example, as disclosed in U.S. Ser. No. 10/623,707 and WO 04/008981, also assigned to the present assignee, and the contents of which are incorporated herein in their entirety, and so on. The dental lab is characterized as being equipped or otherwise able to design part or whole appliances, and/or to partially manufacture or assemble the same, particularly where close tolerances are relatively less critical. On the other hand, while the service center 23 is also equipped to design part or whole appliances, and/or to fully or partially manufacture and/or assemble the same, it is particularly suited to do any of these activities where close or tight tolerances are in fact critical and/or difficult to achieve.

The service centre 23 is a different design and manufacturing entity to the dental lab 26 and is thus separate thereto. However, while the service centre 23 may be located in a different geographical zone to the dental clinic 26, for example, different countries, different cities in the same country, different neighborhoods in the same city, or even different buildings in the same neighborhood, they may also be housed in the same building, and in any case maintain their separate functions and capabilities, as described herein.

Typically, for any given prosthesis, the service center 23 shares at least the manufacturing of the prosthesis with one dental lab 26 according to predetermined criteria, as will be further elaborated herein. Nevertheless, the manufacturing for a particular prosthesis may also be shared between the service center 23 and a number of dental labs 26, each of which contributes a part of the manufacture. The same applies also to the design of the prosthesis, which may be executed at the same or a different dental lab 26, and optionally also shared with the service center 23.

The dental lab 26 is typically located in the same locality as the clinic 22 that it services, though the two may alternatively be geographically remote. Thus, the dental lab 26 and the clinic 22 that it services may both be located in the same building or complex, or in different parts of the same city, or in different cities or countries. However, the dental lab 26 of the invention typically has an established working relationship with the clinic 22, and thus tends to be, generally, within the same city.

Figure 2:
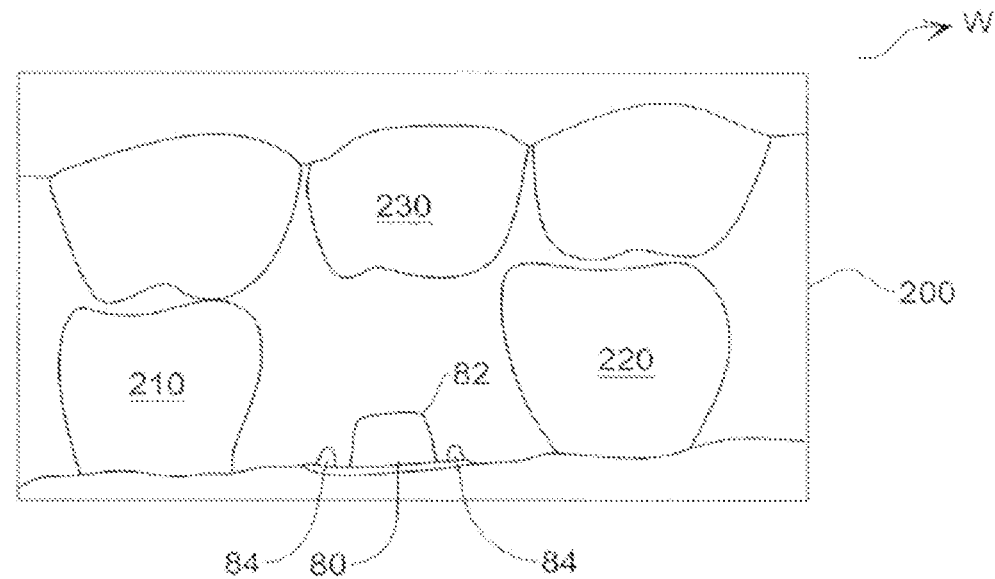
FIG. 2 illustrates a portion of the intra oral cavity of a patient wherein it is desired to implant a prosthesis.
Figure 3:
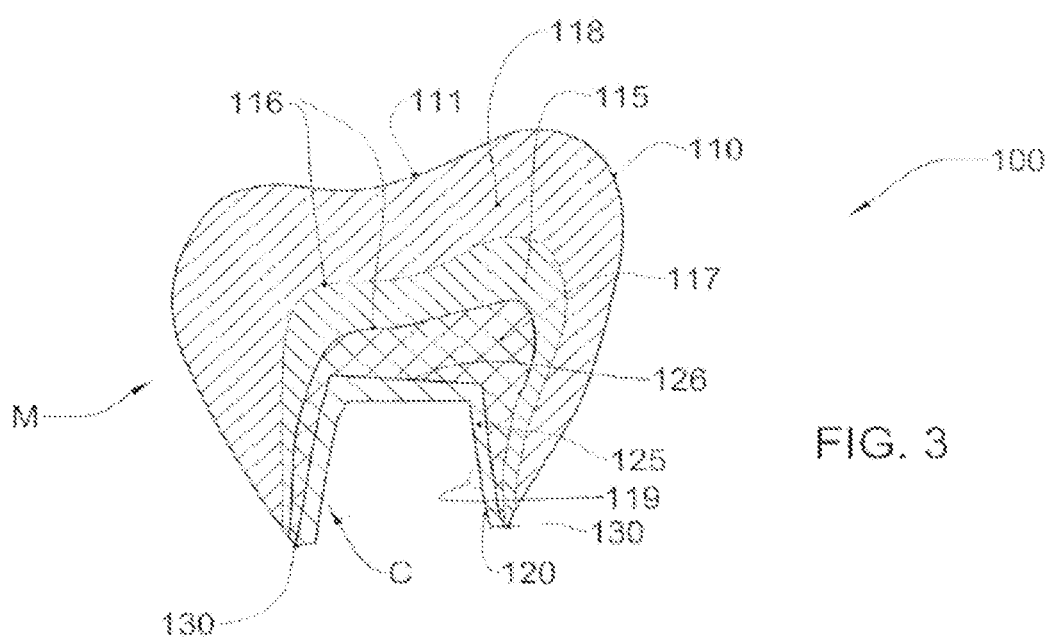
FIG. 3 illustrates in cross sectional view a crown prosthesis having a coping and a multiple layered cap.

In a first embodiment of the present invention, the dental appliance to be manufactured is a prosthesis such as a crown. Referring to FIGS. 2 and 3, such a crown, generally designated 100, has an internal surface 120 and lower edge 130 that needs to be very precisely defined and manufactured to match the preparation 80 and finish line 84, respectively, in the intraoral cavity 200 of a patient. Such a crown typically comprises a cap 110 and a coping 125.

Referring to FIG. 1, the communication network 24 may also used to send a prescription from a clinic 22 and/or dental lab 26 to the service center 23, and/or between the clinic 22 and the dental lab 26, for example when the dental practitioner in the clinic 22 interacts with the dental lab 26 to finalize the prescription for the service center 23. The prescription may include instructions from a dentist at a clinic 22 and/or from the dental lab 26 specifying which of the patient's teeth is to be restored, the material to be used for the restoration (for example, the form and material of the shoulder, whether metal or ceramic shoulders are to be provided in the lingual and buccal parts of the prosthesis, and so on), the color of the required restoration, comments about the margin line (finish line), and so on.

While the term "preparation" refers to the stump left of the tooth that is to be replaced by the crown and on which the crown is to be mounted, it also includes artificial stumps or other devices that may be implanted in the intraoral cavity in such a position or in a position that is optimal for implanting the crown.

The cap 110, which may be formed from a plurality of layers 115, preferably needs to have a natural looking appearance, and thus the color and surface features of the cap 110 need to be matched to those of the other teeth of the intra oral cavity 20, particularly those in proximity to the site in which the crown 100 is to be implanted. Further, the dimensions of the cap have to be such as to enable the crown to fit between the adjacent teeth 210, 220, and to provide proper occlusion with the teeth 230 of the facing jaw. The manufacturing tolerances for the cap 110 are not as tight as for the inner surface 120 and may be of the order of about 80 microns, which is within the capabilities of most regular dental labs 26 that currently provide such services to clinics 22.

The coping 125 is made from a metal, ceramic, or other very strong material, and is designed for taking the mechanical loads of the crown 100 associated with the normal activity of the teeth. The inner surface 120 and lower edge 130 of the coping 125 need to closely match the preparation 80 and finish line 84, and moreover provide a reasonable insertion path for the crown 100. Typically, the fitting tolerance for the internal surface 120 and lower edge 130 needs to be in the order of about 40 microns or less, which is more demanding than for the cap 110. If the dimensional accuracy is not maintained to this tolerance level, there is a risk of infection of the remaining parts of the tooth, the infection entering via the gap between the crown and the preparation, in particular between the lower edge 130 and the finish line 84. Furthermore, where such tolerances are not met, the life of the prosthesis may be severely reduced. Although prior art dental labs do design and manufacture copings, such close tolerances are not typically achievable by most regular dental labs that currently provide such services to clinics. Accordingly, the design and manufacture of the internal surface 120 and lower edge 130 may be advantageously carried out according to the present invention by the service centre 23, which has the equipment and expertise to do so. By centralizing such specialized and accurate work from a number of clinics 22, the service center 23 is able to carry out such work in a more cost effective and efficient manner, and generally more accurately, than the dental lab 26.

Figure 4:
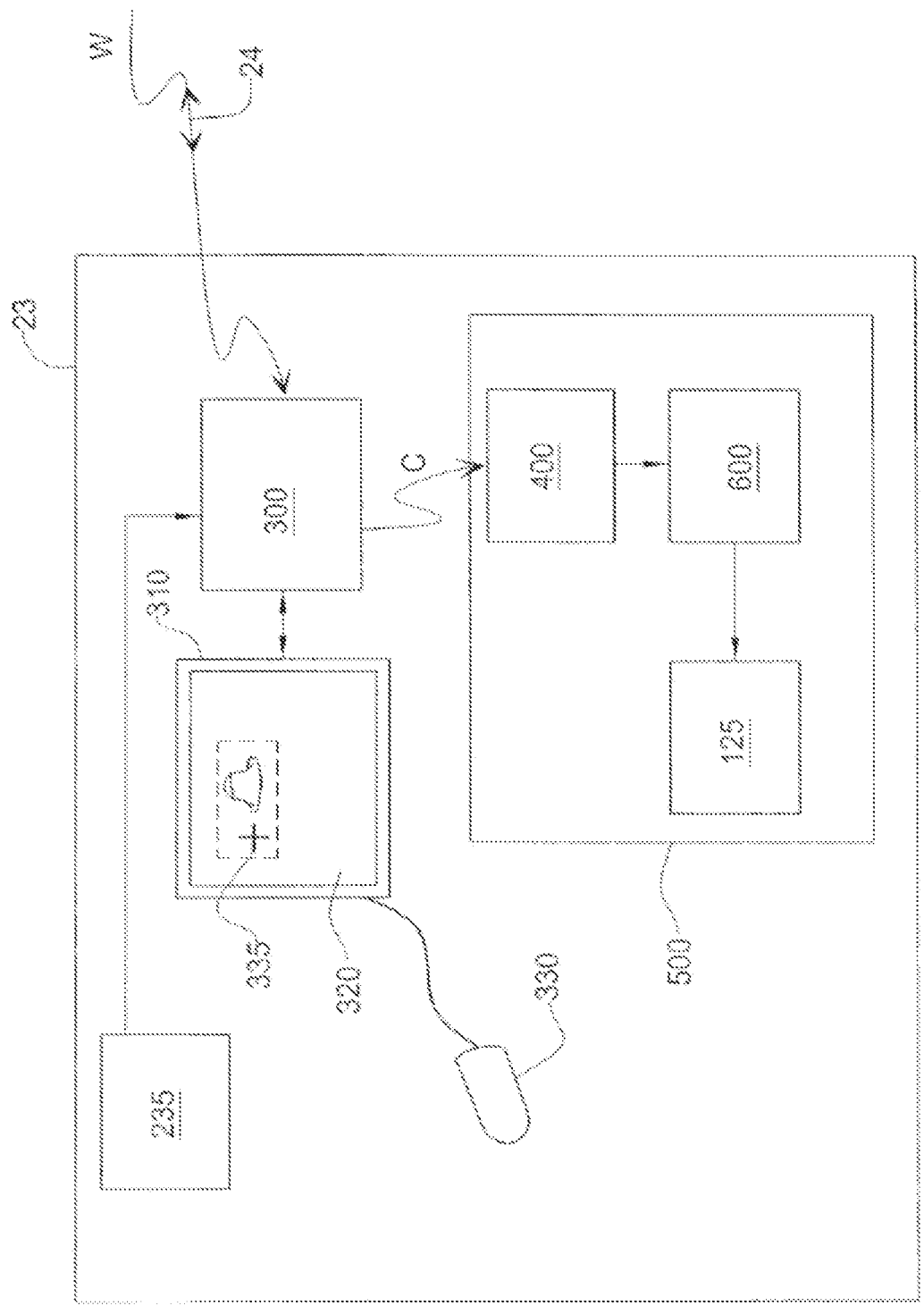
FIG. 4 illustrates a service center according to the first embodiment of the invention.

Referring to FIG. 4 in particular, the service centre 23 comprises suitable hardware such as a server 300 that is suitably programmed to receive the 3D data W of the oral cavity 200, as well as the prescription from the clinic 22 or from the dental lab 26, or possibly the data and the prescription may be provided from a different one of said clinic 22 or dental lab 26. Alternatively, the data W is provided by the server 300 or another computer at the service center 23 which is adapted for providing 3D data from a negative-positive model of the cavity, or by any other means, as described above. The server 300 comprises suitable software to enable the 3D data corresponding to the external surface 82 of the preparation and finish line 84 to be isolated from the rest of the 3D data W of the oral cavity 200, and this may be done in an automated manner. Alternatively, this selection of the data may be done interactively by specialized personnel. Thus, the server 300 optionally comprises at least one monitor or other display means 310 for displaying the 3D data as a manipulable image 320, whereby by means of a mouse 330, keyboard, voice recognition means, or any other suitable user interface the said personnel may choose demarcation points on the image, which in his/her opinion correspond to the finish line. These points may be marked with the help of a cursor 335 or other icon or the like on the display means 310. The server 300 also has suitable software to define the inner surface 120 according to predetermined parameters. These parameters take into account the geometries of the external surface 82 of the preparation 80 and finish line 84, the spacing required between the coping and the preparation to accommodate the adhesive or cement that is used to provide the bond between the two, and also the insertion path geometry, which is a function of the topology of preparation 80 as well as of the adjacent teeth 210, 220. The server 300 also comprises suitable software to automatically or interactively provide the external shape of the coping 135, and thus provide a complete geometrical representation or 3D data C of the coping, digitally. The external surface 126 of the coping 125 may be defined in any number of ways. Typically, at least a majority of the external surface 126 is displaced from the internal surface 120 by a uniform amount to provide an approximately constant thickness throughout. However, the thickness of the coping may vary for a number of reasons. For example, it may be necessary in some cases to provide a coping that is stronger in some parts than in others, reflecting the activity that the crown 100 will be expected to engage in—as a molar, incisor, canine and so on. Also, the preparation may be of such a shape that in some areas relatively little room is left for the coping 125, while in other areas there is a wider gap between the coping and the next tooth. The wider this gap is, the thicker the coping may be, while still permitting sufficient material for the cap 110 to be provided. In cases where the cap 110 is cemented or bonded onto the coping using an adhesive, it may be desired to provide more adhesive between the lower edge of the coping and the cap relative to other parts between the coping and the cap. Accordingly, the outer surface 126 may be somewhat recessed close to the lower edge 130, and thus the coping may be thinner here. The additional adhesive that may be provided at the recess relieves some mechanical stress from the lower edge of the cap 110, which is structurally the weakest part thereof, typically, thus prolonging the life of the crown 100.

The server 300 is further adapted to provide machining instructions to a suitable material removal machine 400, based on the geometrical 3D data C of the coping 125. Alternatively, the server 300 transmits the 3D data C to another computer (not shown) that provides the machining instructions to machine 400. The service center 23 further comprises a suitable manufacturing centre 500 for manufacturing a solid replica corresponding to the 3D data C. Optionally, the manufacturing center 500 comprises said machine 400, which may be adapted for producing a coping 125 directly from a suitable hard material, using the machining instructions. Any suitable machining tool may be used that is adapted for material removal and may include inter alia mechanical tools such as drills for example, laser tools such as for example laser drills or cutters, ultrasonic tools such as for example ultrasonic cutters, and so on. The machining paths and material removal characteristics of such tools can be finely controlled, typically by a control computer comprised in or operatively connected to said machine 400. Thus, the coping may be manufactured directly from the crown material, such as a metal for example, by means of machine 400.

Preferably, the coping is manufactured indirectly, in a manner such as described for example in U.S. Ser. No. 60/459,624 or WO 2004/087000, also assigned to the present assignee, and the contents of which are incorporated herein in their entirety by reference. Essentially, a physical model of the coping is machined from a suitable wax or similar material, by a material removal process using a suitable machining tool and the machine 400, wherein the machining is computer controlled and based on the 3D data C. Then, the wax model is transferred to a casting facility 600, comprised in the manufacturing centre 500, or alternatively provided by a source external to the service center 23, including for example the dental lab 26, and a negative mold of the wax model is produced, typically by a lost-wax process. Thereafter, the mold is used for forming the coping 125, either by flowing a molten metal into the mold and allowing solidification of the metal, or by injecting ceramic powder thereinto and heating the same until the ceramic powder sinters and forms a solid integral unit, or by another suitable method. The mold may then be removed, thereby providing a coping 125 that is dimensionally faithful to the 3D data C to high dimensional accuracy, typically within 40 microns or less.

The wax-based method for producing the coping 125 has some advantages over the direct material removal method, for example less wear and breakage is experienced by the machining tool, and thus lowers costs. Furthermore, deformations of the tool, when a direct contact tool such as for example a mechanical tool is used, is less likely, and thus less deviations from the nominal dimensions (i.e. 3D data C) of the coping 125 occur than when producing a coping directly from a metal or other hard material.

Once the coping 125 has been manufactured, the cap 110 can be bonded thereto, if manufactured separately. Alternatively, and typically, the cap 110 is manufactured already joined to the coping, as will become clearer herein. In either case, the external surface 111 of the cap 110 needs to be defined first. The external surface 111 is such as to provide:

(a) adequate clearance between the crown 100 and adjacent teeth 210, 220 when the crown is fixed onto the corresponding preparation in the intraoral cavity 20; and (b) adequate occlusion between the crown 100 and the teeth 230 of the opposite jaw when the crown 100 is fixed onto the corresponding preparation in the intraoral cavity 20.

At the very least, the external surface 111 of the cap 110 is such as to provide certain critical linear dimensions that comply with at least one of the target width or target height of a site or location on the jaw on which the crown is to be fitted. The target width may include the mesiodistal size of a tooth that is being replaced by the crown, and may be defined such as to provide adequate clearance between the crown and adjacent teeth when the crown is fixed onto the corresponding preparation in the intraoral cavity. The target height may be defined such as to provide adequate occlusion with the "working side" of the tooth and avoiding interfering contact between the crown and teeth of the opposite jaw when the crown is fixed onto the corresponding preparation in the intraoral cavity.

An outer shape for the external surface 111 may be chosen, and this can be accomplished in a number of ways. For example, if the original tooth that the crown 100 is replacing is still available and the outer surface thereof is of a reasonable form, the tooth may be scanned, and the 3D data of the surface obtained. If necessary, this 3D data may be considered as a starting point, and the final shape of the external surface 111 is obtained by manipulating this data as required by the technician or other user that is designing the surface 111. Alternatively, if the patient has a reasonably healthy tooth on the same jaw but on the adjacent quadrant at a position corresponding to where the crown 110 is to be fitted, the 3D data of the surface of this tooth is obtained. Optionally, this tooth may be scanned as described herein to obtain the 3D spatial coordinates thereof, unless this data may already be available from the 3D data of the oral cavity 200 stored in the server 300. Alternatively, a suitable profile for surface 111 may be chosen and obtained from a library 235 that comprises the 3D spatial profiles of shapes or profiles of the outer surfaces of a plurality of crowns and teeth. If necessary, the relative size and shape of the surface 111 may be adjusted by the technician to better match the other teeth in the jaw. Then, the chosen surface is adjusted in any suitable manner, either manually, automatically, interactively or in any other manner, in order that the required target dimensions of surface 111 will fit within a control volume that defines the maximum dimensions of the cap, as required to conform to the space available in the intra oral cavity 200. In particular, the control volume is chosen such as to provide adequate clearance between the crown and adjacent teeth, and adequate occlusion with the opposite teeth, when the crown is properly fixed onto the preparation.

Figure 5:
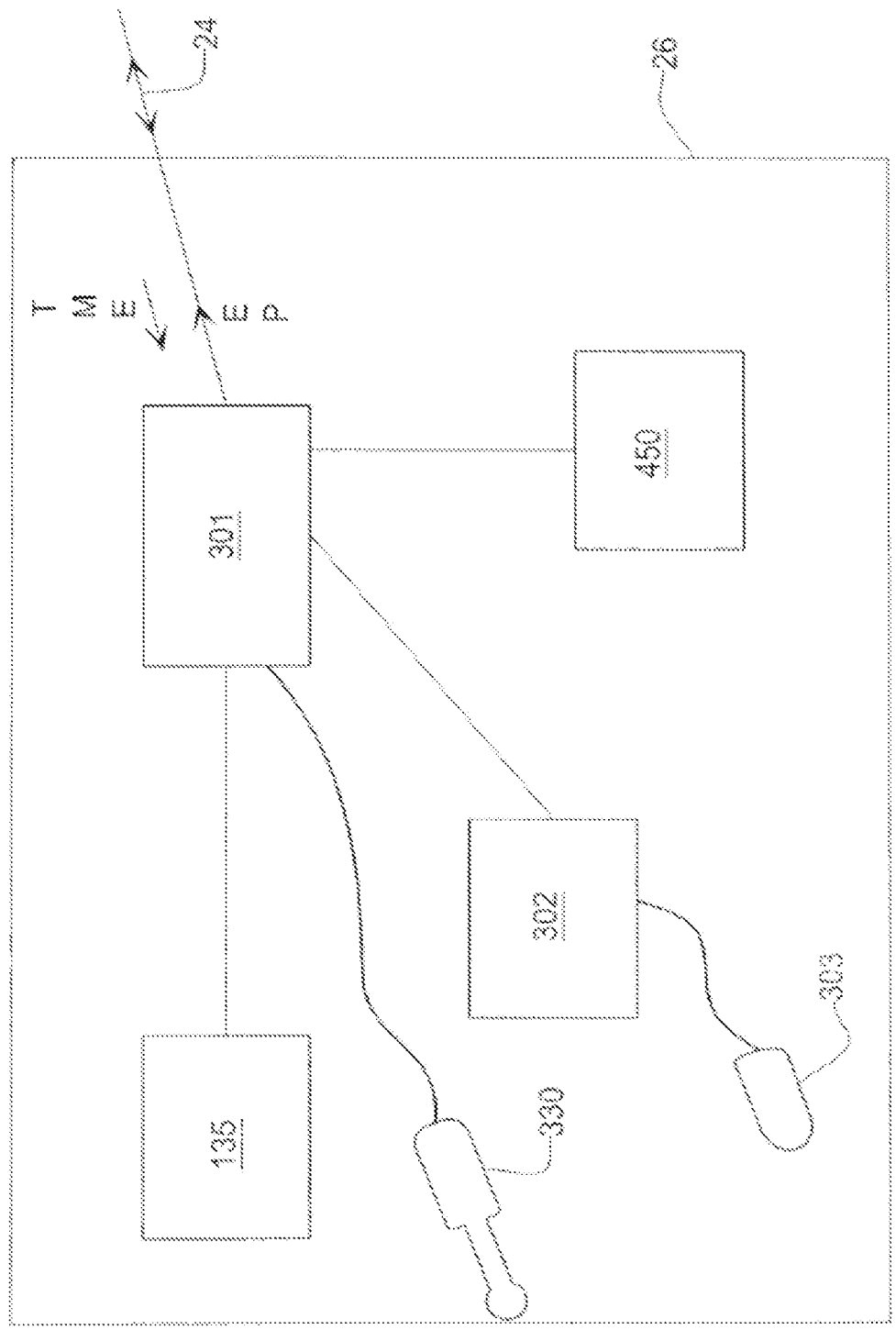
FIG. 5 illustrates a dental lab according to the first embodiment of the invention.

The design of the external surface 111 may be executed at the service center 23 or at the dental lab 26. If at the latter, and if use is made of a library of 3D spatial profiles of shapes or profiles of the outer surfaces of a plurality of crowns and teeth, then the dental lab 26 can make use of library 235 of the service centre 23, via communications network 24. Alternatively, the dental lab 26 may have its own digital library 135 of 3D spatial profiles of shapes or profiles of the outer surfaces of a plurality of crowns and teeth, operatively connected to a local server 301 or other computer, as illustrated in FIG. 5, which comprises a suitable display 302 and user interface 303 such as a mouse and/or keyboard. The local server 301 is in any case in communication with the server 300 of the service center 23 and a computer 32 of the dental clinic 22 via network 24.

Optionally, and according to predetermined criteria, the details, including shape and size of each of the intermediate layers 115 can also be chosen or determined, such as are considered that will provide a particular or desired visual effect, for example. Thus, it may be decided, for example, to provide an outer layer made from an opalescent porcelain, but having a varying thickness, so that at some zones an intermediate layer will appear more reflective than at others. Similarly, an intermediate layer can be made from a suitable porcelain having a desired color, and the depth of this layer can also be varied to provide different hues of the color. For example, at places where the depth of the layer 115 is greater, the layer 115 will appear a little lighter than where the layer is shallower. This aspect of the design of the cap may be executed by the service center 23 or by the dental lab 26.

Once the design of the cap 110 is complete, the next stage, that of manufacturing the cap 110 can begin. As mentioned before, there are at least two methods for manufacturing the cap 110—as a separate item which is then bonded to the coping 125; or together with the coping 125.

In the first method, the inner surface of the cap 110 needs to be defined, and the design takes into account a number of parameters, such as for example the geometry of the external surface 126 of the coping 125, the spacing required between the cap 110 and the coping 125 to accommodate the adhesive or cement that is used to provide the bond between the two. It should be noted that if this method is adopted, it is preferable for the shape of the external surface 126 of the coping to be designed such as to provide an adequate insertion path geometry for the cap 110, which is a function of the external surface 126 as well as of the adjacent teeth 210, 220. Thus, if necessary, a damaged cap may be replaced on a coping 125 that is already cemented on the preparation 80, without having to remove the coping 125 from the preparation 80 and thus avoid possibly damaging the same. Since the 3D data of the cap 110, internally and externally is known, it is possible to manufacture a replacement cap 110 without having to rescan the oral cavity. Alternatively, if the whole crown 100 were to be replaced, the preparation area would need to be rescanned, as the geometry thereof may have changed as a result of removing the coping 125.

The next step is to combine the 3D data of the internal surface of the cap 110 and 3D data of the external surface 111 of the cap 110, to provide a complete 3D digital model M of the cap. The 3D model M may be designed at the dental lab 26 or at the service center 26 itself, using the original 3D information W of the intraoral cavity 20, and particularly the 3D model of the coping 125 that was previously created. Where this activity is executed at the dental lab 26, the corresponding design software in server 300 is accessed by the technician at the lab 26 via the communications network 24. Alternatively, the design software may be comprised in the computer 301 at the dental lab 26, and the required data, including the 3D data C of the coping 110, may be acquired from the service center 23 via the communications network 24. The 3D model M is then converted, preferably by server 300 or alternatively by computer 301, into machining instructions E for machine 400, for example. Thereafter, the cap 110 may be manufactured in any one of a number of ways.

For example, the said machine 400, may be adapted for producing the cap 110 directly from a suitable durable material, using the machining instructions based on model M. As for the coping 125, any suitable machining tool may be used that is adapted for material removal, and may include inter alia mechanical tools such as drills for example, laser tools such as for example laser drills or cutters, ultrasonic tools such as for example ultrasonic cutters, and so on. Preferably, the machining paths and material removal characteristics of such tools can be finely controlled, typically by a control computer operatively connected to or comprised in machine 400.

Alternatively, the cap 110 may be manufactured indirectly, using a wax-loss process similar to that described herein and in U.S. Ser. No. 60/459,624, for the coping, mutatis mutandis. Thus, a physical model of the cap is machined from a suitable wax or similar material, by a material removal process using a suitable machining tool and the machine 400. Then, the wax model is transferred to a casting facility, which may be the same or a different casting facility 600, comprised in the manufacturing centre 500, or alternatively provided by a source external to the service center 23, including for example the dental lab 26, and a negative mold of the wax model is produced, typically by a lost wax process. Thereafter, this mold is used for forming the cap 110, either by flowing a molten metal into the mold and allowing solidification of the metal, or by injecting ceramic powder thereinto and heating the same until the ceramic powder sinters and forms a solid integral unit, or by any other suitable means. The mold may then be removed, thereby providing a cap 110 that is dimensionally faithful to the 3D model M to high dimensional accuracy, typically within about 40 microns or less.

If it is required to manufacture the cap 110 from a plurality of different layers of materials, for example to provide a natural looking appearance that matches the other teeth of the patient, this may be done as follows. First, the 3D model M may used to design the outer shape of the outer surface 116 of each intermediate layer, as illustrated in FIG. 3. The 3D models T, each corresponding to one intermediate layer 115, and of course including the final layer 118 are converted, typically by server 300 or alternatively by computer 301, to material removal instructions P which are executable by a suitable material removal machine such as for example machine 400. Then, the innermost layer 117, i.e., the layer that is to be mounted directly to the coping 110, is manufactured by direct material removal methods or by indirect methods such as a lost-wax process, similar to that described above for the whole cap 110, mutatis mutandis. This stage of the manufacture, since it requires high dimensional accuracy, is preferably carried out at the service center 23. Where an indirect method is used, at least the wax model is manufactured at the service center 23 for the same reason. Then, successive layers 115 of material up to a final layer 118 may be added to the inner layer 117, in a manner known in the art, and each layer is subjected to a material removal operation so that the external surface 116 thereof matches the design geometry, i.e., 3D data T. The dimensional accuracy of the surfaces 116 can be 80 microns or less, and that of external surface 111 of the cap 110, i.e., of the final layer 118, is preferably about 80 microns, and thus, the material removal operations for the intermediate and final layers may be advantageously carried out at the dental lab 26.

In the second method, the cap 110 is produced already joined with the coping 125, i.e. starting with a workpiece comprising the coping 125. Essentially, a layer of suitable crown material is added to the coping 125 in a manner known in the art, and this layer is then subjected to a material removal operation to provide the desired profile for the external surface 111, for example in a manual fashion, as is well know in the art, or alternatively in a computer controlled manner, for example similar to that as described above for the separate cap, mutatis mutandis.

Thus, there is no need in this embodiment to define an inner surface for the cap 110, since material is applied directly to the coping 125, automatically assuming the appropriate shape over the coping's outer surface, and therefore high dimensional accuracy between the cap 110 and coping 125 is automatically achieved.

Where it is desired to manufacture the crown in which the cap 110 comprises a plurality of layers 115 including a final layer 118, for each layer suitable crown material may be added to the previous finished layer and subsequently machined or otherwise subjected to a material removal operation, manually or computer-aided, to provide the required profile for each external surface 116 of the layers, including the outer surface 111 of the cap 110.

When the crown is fabricated in the traditional fashion at the dental lab 26, including one or more material layers built up over the coping manufactured by the service center 23, there is less need for the outer surfaces of each layer to be precisely defined in a virtual model. Thus in such cases the technician at the dental lab 26 may design the cap 110 in any suitable manner, including traditional methods or any other method, including manual, interactive of automated methods, or a combination of two or more thereof For the first and second methods described above, the material removal operations for the innermost layer 117, intermediate layers 115 and final layer 118 can be performed at the dental lab 26, which comprises a suitable material removal machine 450 comprising any suitable machining tool that is adapted for material removal, and may include inter alia mechanical tools such as drills for example, laser tools such as for example laser drills or cutters, ultrasonic tools such as for example ultrasonic cutters, and so on. Preferably, the machining paths and material removal characteristics of such tools can be finely controlled, typically by a control computer operatively connected to or comprised in machine 450 in which the machining instructions P, previously prepared, are stored. Alternatively, the material removal operations are carried out in the dental lab 26 using more traditional methods. Particularly for this purpose, a physical positive model of the teeth, particularly including the preparation and surrounding teeth including the adjacent teeth and the facing teeth of the opposite jaw, is provided to the dental lab 26, which assists the technician in fabricating the full prosthesis. Such a physical model can be made from the virtual model W using any suitable method, such as for example material removal methods including CNC machining methods, or using other techniques, for example prototyping methods, typically at the service center 23, though optionally at the dental lab 26. Alternatively, and particularly if a negative model was used to obtain the virtual model in the first place, the positive model may be produced directly from the negative model in a manner known in the art.

It should be noted that when the manufacture of the external surfaces 116 of the layers 117, 115 and 118 of the coping 110 is conducted in a different machine to that used for the manufacture of the internal surface of the cap 110 (in the case of the first method) or of the coping 125 (in case of the second method), proper spatial alignment between the internal surface and the external surfaces of each component must be maintained. This may be achieved in a number of ways. For example, surface features such as projections 119 of a known geometry and located at a known position in inner surface 120 (or elsewhere) are included in the 3 model M, and thus also included in the physical coping 125 that is manufactured. The projections 119 are used as reference datums when the coping is moved to a different machine such as machine 450 to continue with the manufacture of the crown. When the cap 110 is manufactured separately from the coping 125, similar projections may be included in the cap 110, also serving as a reference datum for aligning the cap 110 with respect to the coping 125. Alternatively, once the coping 125 and mounted in the next machine, such as machine 450, the outer surface thereof is scanned by means of a suitable scanner, for example scanner 330, and the 3D data thus obtained is used by computer 301 to adjust the material removal instructions P such as to align the outer surface of the cap 110 with the coping 125.

Preferably, the material removal operations, for either the first or second methods, is carried out according to the method disclosed in U.S. Ser. No. 60/542,327, entitled "METHOD AND SYSTEM FOR MANUFACTURING A DENTAL PROSTHESIS", filed on 9 Feb. 2004, also assigned to the present assignee, and the contents of which are incorporated herein by reference thereto. Essentially, the crown 100 may be manufactured by performing a mapping operation to determine the three-dimensional shape of the outer surface of the material that is to be machined to form the crown 100, either the final layer 118 or any intermediate layer 115, including the inner layer 117, and then subjecting the layer to a material removing operation, wherein the machining paths are computer controlled on the basis of the local differences between actual and required shape, and optimized to reduce machining times. Alternatively, the crown 100 is manufactured by performing a measuring operation to determine at least some critical dimensions of the outer surface 111 of the prosthesis, either the final layer or any intermediate layer. These measurements are then compared to the corresponding nominal dimensions in which the crown is to be fitted, and then subjecting the layer to a material removing operation, wherein the machining paths are computer controlled and optimized to reduce machining times.

Accordingly, the distance between adjacent machining paths may be maintained, for example in the order of 0.02-0.2 mm, and an optimal amount of material can be removed in each sweep without damaging the prosthesis and/or the tool. There is therefore no need to arrange machining paths within a fictitious envelope, as these paths are designed to match the actual external details of the workpiece, i.e. the material layer before machining commences. Thus:

potential damage to the crown and/or tool by attempting to remove too much material in one sweep, as may happen if the material exceeds the limits of the envelope, is generally avoided; and,
  machining time is not wasted by passing the tool across empty air for some portion of the machining paths, as may happen if the material is well below the limits of the envelope.

According to this manufacturing process, then, for each layer that is added to the coping 125 (for the said second method) or to the innermost layer 117 (for the said first method, and thus also including the innermost layer 117 itself):

a) actual dimensional data for at least one parameter associated with said layer is obtained;
  b) for at least one such parameter, a comparison is made between the actual dimensional data and predetermined target dimensional data that it is desired to conform said parameter to; and
  c) the layer is then subjected to a material removal operation by suitable machining means along machining paths which are a function of said comparison, such that after said operation the parameter associated with the layer substantially conforms with said target dimensional data.

The parameter is preferably a geometric parameter comprising surface coordinates of each layer, while the target dimensional data comprises the numerical values of the surface coordinates of an idealized or required outer surface of the prosthesis. The surface coordinates of said required outer surface are provided by the 3D models T.

The aforesaid actual dimensional data may comprise the actual surface coordinates of each layer prior to the material removal operation. In step (a) the layer is scanned with a suitable three-dimensional surface probe 330, typically comprised and used in said dental lab 26, and operatively connected to the computer 301. Such a probe preferably provides a three-dimensional structure based on confocal imaging. Alternatively, the actual dimensional data may be obtained using any suitable intra oral scanning technique, based on optical methods, direct contact or any other means, applied directly to the patient's dentition. Alternatively, the data may be obtained using techniques based on scanning a positive and/or negative model of the intra oral cavity. Alternatively, X-ray based, CT based, MRI based, or any other type of scanning of the patient or of a positive and/or negative model of the intra-oral cavity. The dimensional data may be associated with a complete dentition, or of a partial dentition, for example such as the preparation only, and corresponds to 3D data W.

Alternatively, the aforesaid parameter is a geometric parameter comprising at least one linear dimension of said layer. The target dimensional data thus comprises the numerical values of at least one of the target width or target height of a location on the jaw on which the crown is to be fitted. The target width may include the mesiodistal size of a tooth that is being replaced for example and may be defined such as to provide adequate clearance between the crown and adjacent teeth when the prosthesis is fixed onto the corresponding preparation in the intraoral cavity. The target height may be defined such as to provide adequate occlusion between said prosthesis and teeth of the opposite jaw when the prosthesis is fixed onto the corresponding preparation in the intraoral cavity.

Figure 6:
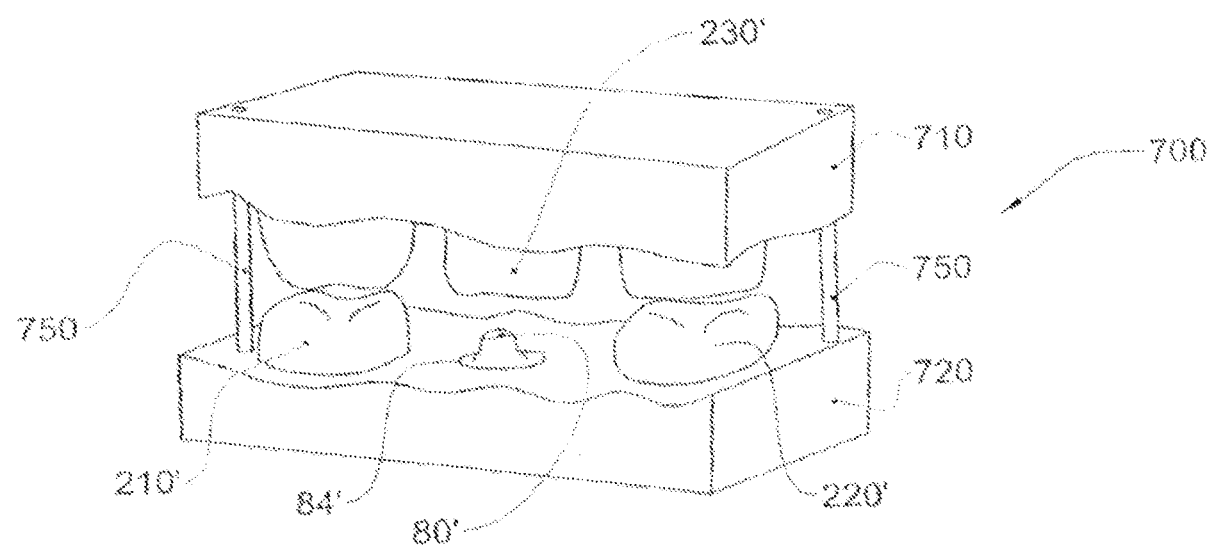
FIG. 6 illustrates a physical model of the intra-oral cavity of FIG. 2.

Referring to FIG. 6, the dental clinic 26 may also be provided with a physical model 700 of the part of the intra oral cavity of interest, namely comprising scale replicas the adjacent teeth 210, 220, preparation 80 and finish line 84, and upper teeth 230 opposite the preparation and the adjacent teeth, shown as 210', 220', 80', 84' and 230' in this figure. The model 700 is in two parts, an upper part 710 and a lower part 720 corresponding to the upper jaw and lower jaw, respectively and joined together reversibly in the correct occlusal relationship by means of alignment pins 750. The model 700 is preferably manufactured by the service centre 23 by any suitable means, for example via CNC machining of two solid blocks of a plaster or other material. The 3D data W that was originally taken from the intra oral cavity 20 is used for providing material removal instructions to machine 400, which can then manufacture the model 700 therefrom. The model 700 is then shipped to the dental lab 23, and helps the technician there to undertake fitting tests of the crown 100 with respect to the preparation 80' and finish line 84' in the model, before the finished crown 100 is finally sent from the dental lab 26 to the clinic 22 for implantation into the intra oral cavity 20 of the patient. Alternatively, particularly when the crown is built up on the coping using traditional methods, the model 700 may be used by the technician for designing and fabricating each of the successive layers of the cap, or when consisting of single layer, the design and fabrication thereof.

Figure 7:
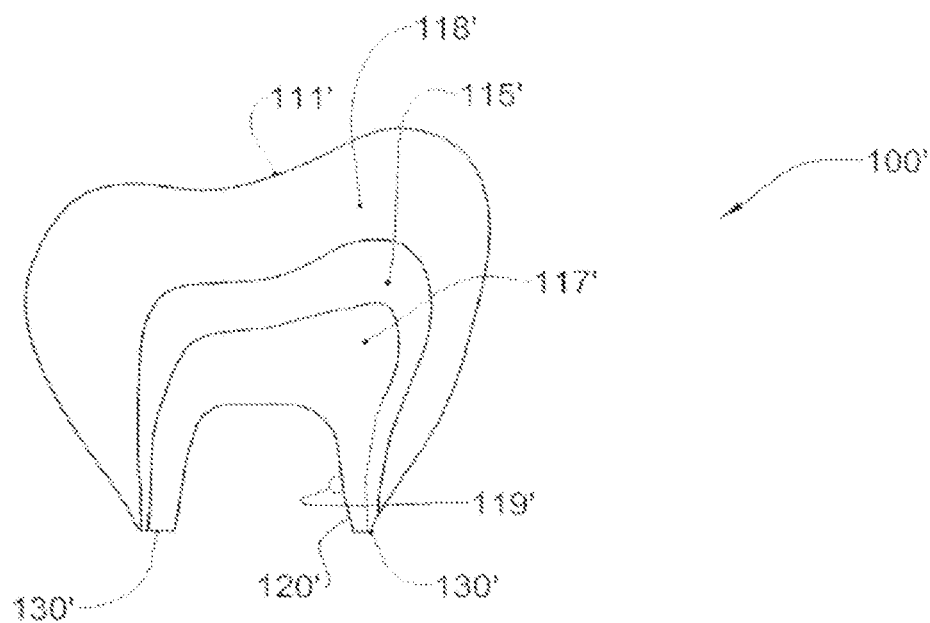
FIG. 7 illustrates in cross sectional view a crown prosthesis having a multiple layered construction.
Figure 8:
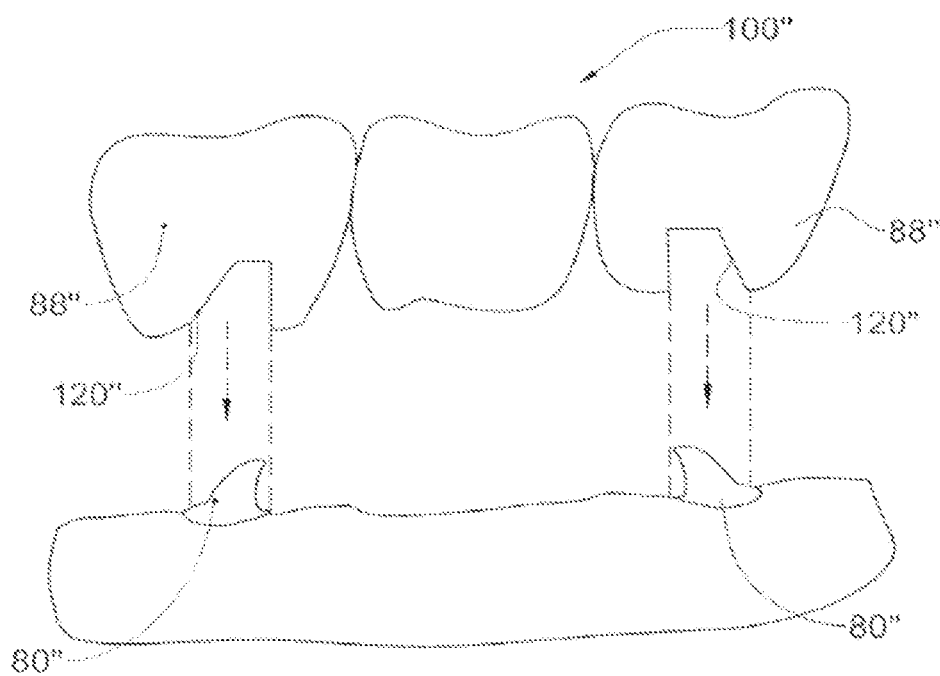
FIG. 8 illustrates the insertion path of a bridge prosthesis according to the invention.

Alternatively, the crown may be manufactured as a monolithic item, wherein the coping as such is not included as a separate item. Thus, referring to FIG. 7, the internal surface of such a crown 100' is required to fit over the preparation 80, and is thus designed and manufactured in a similar manner to the internal surface 120 of the coping 125 as described herein, mutatis mutandis, using direct material removal methods or indirect methods. Similarly, the external surface 111' is designed in a similar manner to external surface 111 of the cap 110, as described herein mutatis mutandis. The manufacture of the external surface 111' may be carried out at the service center 23, optionally concurrently with the manufacture of the internal surface 120' and lower edge 130'. However, it is also possible to send the unfinished crown 100', after the internal surface 120' and lower edge 130' thereof have been prepared by the service centre 23, to a dental lab 26, for a technician thereat to complete the manufacture of the external surface 111', in a similar manner as described herein for external surface 111, mutatis mutandis. The crown 100' may be made from number of layers, 118', 115', 117' and these may each be designed and manufactured in a similar manner to that described for crown 100, mutatis mutandis. However, it is important for the proper spatial relationship between the internal surface 120 and the external surface 111' to be maintained. For this purpose, the crown 100' may be mounted onto an alignment jig before the internal surface material removal operations begin. When the unfinished crown is shipped to the dental lab 26 it is transferred together with the jig, which maintains a known alignment with the manufacturing center 600 of the dental lab 26. Alternatively, the alignment may be achieved in other ways. For example, surface features such as projections 119' of a known geometry and located at a known position in inner surface 120' (or elsewhere) are included. The projections 119' are used as reference datums when the coping is moved to a different machine such as machine 450 to continue with the manufacture of the crown 100'. Optionally, such an alignment jig may comprise said model 700 of part or all of the dentition. Alternatively, once the crown 100' is mounted in the next machine, such as machine 450, the inner surface thereof is scanned by means of a suitable scanner, for example scanner 330, and the 3D data thus obtained is used by computer 301 to adjust the material removal instructions such as to align the inner surface of the crown 100' with the outer surface thereof While the design and manufacture of a crown prosthesis has been described, similar methods may be employed mutatis mutandis to design and manufacture any other dental prosthesis, including bridges, for example, and inlays, such as caps, for example, and any other artificial partial or complete denture. However, and referring to FIG. 8, when designing a bridge 100", care must be taken that the internal contact surfaces 120" for the abutment teeth 88" each provide an adequate insertion path 87" with respect to the preparations 80", taking into consideration the bridge 100" as a whole, and thus that the two paths 87" must be substantially parallel.

While the design and manufacture of a prosthesis has been described, based on a representation of surface information, the three dimensional entities in the oral cavity, such as for example the teeth gums and so on, and also the 3D entities that are designed by the system 10, including the coping 125 and cap 110, for example, may be described instead by solid representations.

In a second embodiment of the invention, the system 10 is used for orthodontical applications. The 3D data corresponding to the patient's intra oral cavity 20 is determined as for the first embodiment, mutatis mutandis. Referring to FIG. 1, the communication network 24 may also used to send a prescription from a clinic 22 to the service center 23. The prescription may include instructions from a dentist at a clinic 22 specifying which of the patient's teeth are to be moved in a dental treatment, as well as the desired final teeth positions at to be attained at the conclusion of the dental treatment.

The service center 23 executes a dental treatment planning software program at a computer station 16 having a central processing unit, such as a personal computer. The software imports the 3D digital data indicative of the patient's teeth previously obtained, and possibly a prescription sent from one of the dental clinics 22. The software processes the 3D data to generate a 3D computer model 18 of the dentition that is displayed to a user on a monitor 20. The treatment planning software includes features to enable the user to manipulate the model 18 to select or design dental appliances for the patient to execute the treatment specified in a prescription sent from the clinic. For example, the user can select or custom design one or more dental appliances (e.g. brackets or archwires) and apply virtual models of these appliances to the 3D model of the teeth. In the case of orthodontic appliances, the software may be configured to move the virtual teeth in accordance with predetermined rules based upon the applied appliances in order to simulate the movement of the teeth that would occur in an orthodontic treatment in which the appliances are applied to the patient's actual teeth. The user then determines whether the selected dental or orthodontic appliances are satisfactory. If not, the user selects new appliances and repeats the process until satisfactory appliances are found.

When the user has determined that the selected dental appliances are satisfactory, the user may send one or more images indicative of the patient's teeth with the selected appliances applied to the teeth to the clinic 22 and request confirmation of the selection from the dentist. Information regarding the patient and the determined appliances are then sent over the communications medium to one of the appliance service centers 23. The dentist may specify to which one of the dental labs 26 the information is to be sent. Each dental lab includes equipment for manufacturing custom made dental appliances such as brackets, archwires, etc. The appliance service center 23 then manufactures the determined appliances and dispatches the appliances to the clinic 22.

Figure 9:
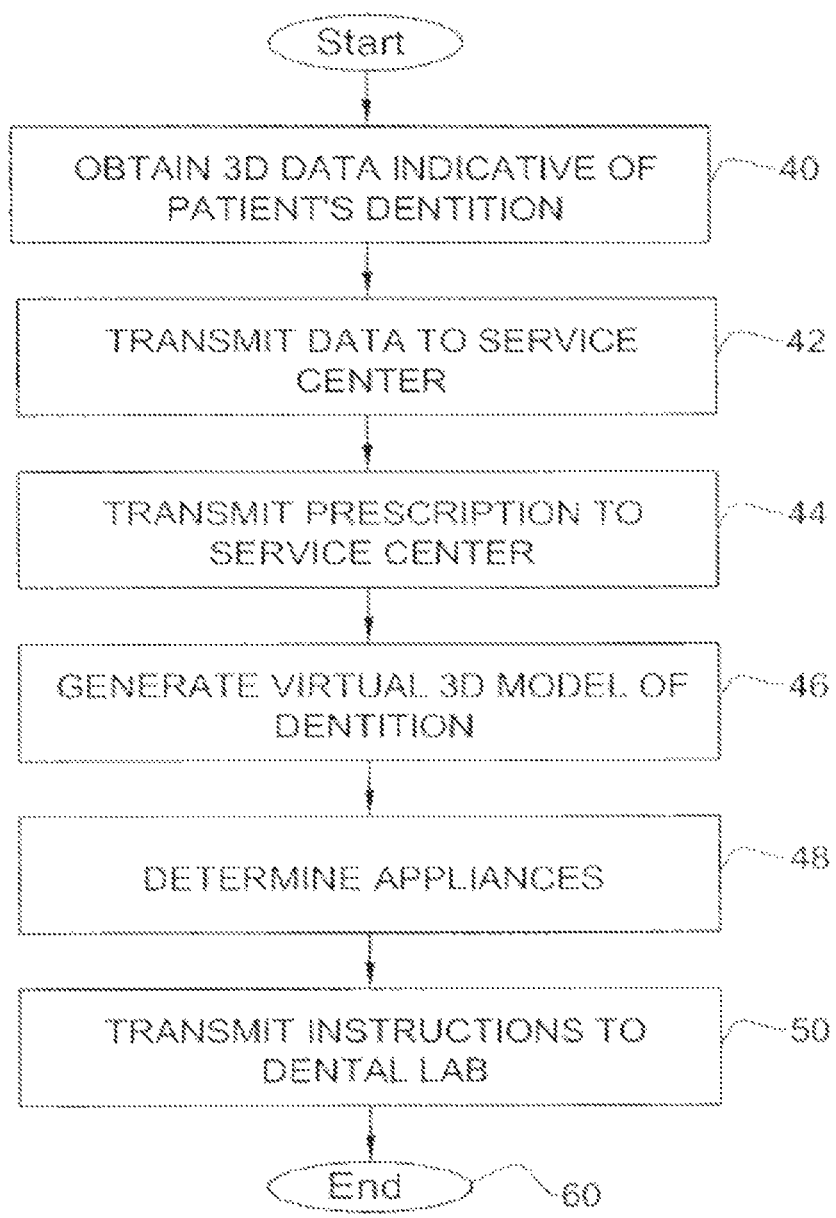
FIG. 9 shows a method for designing and producing dental appliances in accordance with a second embodiment of the invention.

FIG. 9 shows a method for designing and producing dental appliances, in accordance with another aspect of the invention. In step 40, 3D data indicative of a patient's dentition is acquired. As explained above, the data may be acquired either by scanning the patient's teeth directly, or by other methods such as for example scanning a physical model of the teeth. The acquired data are then transmitted to a dental service center (step 42). In step 44, a prescription is sent from a dental clinic to the service center specifying the teeth that are to be moved in a dental treatment, as well as the final position of the teeth at the conclusion of the treatment. Then, in step 46, the service center executes computer software to generate from the acquired data a virtual 3D model of the patient's dentition. The virtual model is used to determine the dental appliances that are required to execute the dental treatment specified in the prescription (step 48). Finally, in step 50, a list of the determined appliances is transmitted to a dental lab 26 where the appliances are made.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for manufacturing an orthodontic dental appliance, comprising:
    receiving, at a service center and from a dental clinic, three-dimensional data indicative of a patient's teeth in a first arrangement,
        wherein the service center is at a first geographic location, and
        wherein the dental clinic is at a second geographic location remote from the first geographic location;
    designing, at the service center, the orthodontic dental appliance based at least in part on the three-dimensional data,
        wherein the orthodontic dental appliance is configured to move at least one tooth of the patient's teeth from the first arrangement towards a target arrangement;
    generating, from the service center, instructions for fabrication of the orthodontic dental appliance;
    transmitting, by the service center and to a dental lab, the instructions for fabrication of the orthodontic appliance,
        wherein the dental lab is at a third geographic location remote from both the first geographic location and the second geographic location.

2. The method of claim 1, further comprising receiving, at the service center from the dental clinic, an orthodontic prescription for the patient's teeth.

3. The method of claim 2, wherein the orthodontic prescription specifies which of the patient's teeth are to be moved.

4. The method of claim 2, wherein the orthodontic prescription comprises information for the target arrangement of the patient's teeth.

5. The method of claim 1, wherein designing the orthodontic dental appliance comprises generating a three-dimensional digital model based on the three-dimensional data received.

6. The method of claim 5, wherein designing the orthodontic dental appliance further comprises displaying the three-dimensional digital model on a monitor.

7. The method of claim 5, wherein the three-dimensional digital model is configured for manipulation by a user on a monitor.

8. The method of claim 5 wherein generating the three-dimensional model comprises identifying an external surface shape geometry of a dentition.

9. The method of claim 5, wherein designing the orthodontic dental appliance comprises applying a virtual model of the orthodontic dental appliance to the three-dimensional digital model.

10. The method of claim 9, further comprising simulating the movement of teeth that would occur in an orthodontic dental treatment using the virtual model of the orthodontic dental appliance.

11. The method of claim 1, wherein designing the orthodontic dental appliance comprises receiving a user input at the service center.

12. The method of claim 11, further comprising modifying the orthodontic dental appliance based on the user input received.

13. The method of claim 1, wherein the instructions for fabrication of the orthodontic appliance comprises a material removal process.

14. The method of claim 1, further comprising fabricating the orthodontic dental appliance based on the instructions for fabrication.

15. The method of claim 14, wherein fabricating the orthodontic dental appliance occurs at the dental lab.

16. The method of claim 14, further comprising providing the fabricated orthodontic dental appliance to the dental clinic for treatment of teeth of the patient.

17. The method of claim 1, further comprising generating, at the service center, a proposed treatment plan to move the at least one tooth of the patient's teeth from the first arrangement towards the target arrangement.

18. The method of claim 17, wherein the proposed treatment plan comprises one or more images indicative of the patient's teeth with the orthodontic dental appliance applied to the teeth.

19. The method of claim 17, further comprising transmitting, by the service center to the dental clinic, the proposed treatment plan for approval.

20. The method of claim 19, further comprising receiving, at the service center from the dental clinic, an approval of the proposed treatment plan.

* * * * *